United States Patent
Collins

(10) Patent No.: US 12,139,981 B2
(45) Date of Patent: Nov. 12, 2024

(54) DRILLING FLUID FLOWBACK TRACKING SYSTEM AND METHOD

(71) Applicant: Kyle Collins, Harper, TX (US)

(72) Inventor: Kyle Collins, Harper, TX (US)

( * ) Notice: Subject to any disclaimer, the term of this patent is extended or adjusted under 35 U.S.C. 154(b) by 0 days.

(21) Appl. No.: 18/206,306

(22) Filed: Jun. 6, 2023

(65) Prior Publication Data

US 2023/0313623 A1    Oct. 5, 2023

Related U.S. Application Data

(63) Continuation of application No. 17/227,224, filed on Apr. 9, 2021, now Pat. No. 11,708,732.

(51) Int. Cl.

| | | |
|---|---|---|
| *E21B 21/08* | (2006.01) |
| *E21B 21/01* | (2006.01) |
| *G01F 1/00* | (2022.01) |
| *G01K 13/02* | (2021.01) |
| *G01L 19/00* | (2006.01) |
| *G01N 11/00* | (2006.01) |
| *G01N 33/28* | (2006.01) |

(52) U.S. Cl.
CPC .............. *E21B 21/08* (2013.01); *E21B 21/01* (2013.01); *G01F 1/00* (2013.01); *G01K 13/026* (2021.01); *G01L 19/00* (2013.01); *G01N 11/00* (2013.01); *G01N 33/2823* (2013.01)

(58) Field of Classification Search
CPC ............ E21B 21/08; E21B 21/01; G01F 1/00; G01K 13/026; G01N 11/00; G01N 33/2823
See application file for complete search history.

(56) References Cited

U.S. PATENT DOCUMENTS

| | | | |
|---|---|---|---|
| 9,574,442 B1* | 2/2017 | McCoy | ................. E21B 47/047 |
| 2014/0128295 A1* | 5/2014 | Wagles | .................... C09K 8/08 |
| | | | 507/111 |
| 2018/0202890 A1* | 7/2018 | Mutch | ..................... G01M 3/28 |
| 2019/0093468 A1* | 3/2019 | Aguirre | ................... E21B 44/00 |

* cited by examiner

*Primary Examiner* — Kristina M Deherrera
*Assistant Examiner* — Jean F Morello
(74) *Attorney, Agent, or Firm* — KEATY LAW FIRM LLC; Thomas S. Keaty

(57) ABSTRACT

A drilling fluid flowback tracking system and method for determining quantities and qualities of drilling fluid returned from the wellhead in drilling operations, providing a frame, a receiving pipe, a riser pipe, and a surge suppressor for conveying returned drilling fluid, a tapered fluid bin having a calibrated drain slot, which retains fluid at a level corresponding to the inflow rate of the fluid, and flow rate marks for visual correlation of the highest level of outflow with the flow rate of the inflow. Collection and retention of data is further provided through sensors in an inline sensor housing communicating through a data cable with a data collection unit. Remote access to the data collection unit is further provided through a data transceiver and remote data unit.

9 Claims, 6 Drawing Sheets

DRILLING FLUID FLOWBACK TRACKING SYSTEM AND METHOD

CROSS-REFERENCE TO RELATED APPLICATION

This application is a continuation of co-pending application Ser. No. 17/227,224, filed on Apr. 9, 2021, the full disclosure of which is incorporated by reference herein and priority of which is hereby claimed.

BACKGROUND OF THE INVENTION

This invention provides a drilling fluid flowback tracking system and method for determining quantities and qualities of drilling fluid returned from the wellhead in drilling operations.

In drilling operations, including workover operations, water-based drilling fluid or drilling mud is pumped down the well under pressure and returns up the annulus to the wellhead, where the quantities and qualities of the returned drilling fluid are measured and analyzed in comparison with the drilling fluid pumped into the well. The return of less fluid than was pumped in might indicate loss of fluid into a void, and the return of excess fluid might indicate an intrusion of fluid, gas, or material. Lack of real-time, on-site awareness of the quantities and qualities of returned drilling fluid can lead to inefficiencies or even outright mistakes in operations. Returned drilling fluid must be dealt with on a nearly continuous basis. Suitable drilling fluid might be re-used, or the water might be separated and re-used. Returned drilling fluid or its components might be hauled away for off-site recycling or disposal, and the operator might pay for such removal based on volume. Lack of captured and recorded data can also lead to inefficiencies, mistakes, or over-billing for recycling or removal.

Because the returned drilling fluid is conveyed in pipe, under pressure, and because the returned fluid is subject to the intrusion of other fluids and gasses, the discharge of returned drilling fluid into tanks or ponds is subject to dangerous bumps or spikes in pressure, which can be hazardous to personnel and to equipment.

What is needed is a system and method for determining the rate of flow and other qualities of returned drilling fluid in real time, and conveying that information immediately to the persons needing to know that information.

US Patent Application Publication No. 2012/0109526 for a "Method and System for Evaluating Sensor Data From A Well Service Rig," published on May 3, 2012 by inventors Lynn W. Conine et al., discloses sensors that receive data and transmit same to a computer or database for storage as activities are completed at a well service rig. The sensor data, including the time it takes to complete particular activities on the rig, is evaluated to determine benchmarks. For example, data from multiple instances of an activity is organized and evaluated to determine the median value for data in that activity. Outlier data is removed and the new median and moving range is determined. A natural process limit range is then determined based on the moving range and data for each instance is compared to the natural process limit range. Instances that have data outside of the natural process limit range are noted and go through supplemental analysis to determine why the data was outside of the natural process limit range. The data can also be evaluated against activity benchmarks to determine if an activity was completed properly.

US Patent Application Publication No. 2012/0274664 for a "Mobile Device Application for Oilfield Data Visualization," published on Nov. 1, 2012 by inventor Marc Fagnou, discloses a mobile device that provides visualization and manipulation of well data generated from one or more well sites. The well data is collected, stored, and aggregated on one or more aggregated data servers. The mobile device includes a touch screen display, a communication interface, and a processor operatively connected to the touch screen display and the communication interface. The processor is configured to receive well data from the one or more aggregated data servers via the communication interface and display a user interface on the touch screen display that graphically displays elements of the well data. The processor is further configured to receive user inputs from the touch screen display and update the displayed well data on the graphical display based the user inputs received on the touch screen display.

U.S. Pat. No. 9,074,468 for a "Method for Real-Time Streaming of Well Logging Data with Self-Aligning Satellites," issued on Jul. 7, 2015 to assignee SELMAN AND ASSOCIATES, LTD., provides for a method for providing real-time streaming drilling data transmission services using self-aligning satellites. The method can include receiving and transmitting the drilling data using client devices, radio boxes, a processor, a local network, a satellite network, a router and switch, a satellite modem, and self-aligning satellite dishes. The drilling data can be transmitted to a remote network operation center and a remote central server. The remote central server can real-time stream the remote client devices.

U.S. Pat. No. 5,732,776 for a "Downhole Production Well Control System and Method," issued on Mar. 31, 1998 to assignee Baker Hughes Incorporated, provides for a downhole production well control system for automatically controlling downhole tools in response to sensed selected downhole parameters. An important feature of this invention is that the automatic control is initiated downhole without an initial control signal from the surface or from some other external source. This control system generally comprises downhole sensors, downhole electromechanical devices, and downhole computerized control electronics whereby the control electronics automatically control the electromechanical devices based on input from the downhole sensors. Thus, using the downhole sensors, the downhole computerized control system will monitor actual downhole parameters (such as pressure, temperature, flow, gas influx, etc.) and automatically execute control instructions when the monitored downhole parameters are outside a selected operating range (e.g., indicating an unsafe condition). The automatic control instructions will then cause an electromechanical control device (such as a valve) to actuate a suitable tool (for example, actuate a sliding sleeve or packer; or close a pump or other fluid flow device). The downhole control system of this invention also includes transceivers for two-way communication with the surface as well as a telemetry device for communicating from the surface of the production well to a remote location.

US Patent Application Publication No. 2019/0309621 for a "Drilling Communication System with Wi-Fi Wet Connect," published on Oct. 10, 2019 by applicant Nabors Drilling Technologies USA, Inc., discloses drilling communication systems that employ a Wi-Fi wet connect to communicate information from one downhole subsystem to another. In some implementations, the subsystems are disposed within drilling callers making-up a bottom hole assembly (BHA). The Wi-Fi wet connect may communicate information obtained by a first downhole subsystem for storing or transmission by the second downhole subsystem.

US Patent Application Publication No. 2018/0285515 for a "System and Method for Automated-Inflow Control Device Design," published on Oct. 4, 2018 by applicant Saudi Arabian Oil Company, discloses a system and method for designing automated inflow control devices to be used in the extraction of hydrocarbons from subterranean formations. According to at least one embodiment, the system includes real-time data processing module configured to gather and process well data, the well data comprising logging while drilling data and user inputted data, and an intelligent field restriction module configured to generate one or more optimized inflow control device designs based on the well data gathered and processed by the real-time data processing module. The system further includes an inflow control design module configured to couple the one or more optimized inflow control device designs from the intelligent field restriction module with one or more scenarios to create a set of ranked optimized inflow control device designs, from which a user selects a preferred optimized inflow control device design based on well optimization goals defined in the user inputted data.

U.S. Pat. No. 9,080,438 for a "Wireless Well Fluid Extraction Monitoring System," issued on Jul. 14, 2015 to inventors James N. McCoy, provides for a system for wirelessly monitoring a well fluid extraction process, which operates in conjunction with a host computer. The system includes a wireless base that has a base radio and a communication port to interface with the host computer. The system also has a first remote with a first remote radio that communicates with the base radio using a radio protocol. The first remote also has a first sensor interface that can receive a first sensor signal. The first remote digitally samples the first sensor signal at a predetermined sampling rate, and then communicates first sampled data to the wireless base through the radio protocol. A host software application, which executes on the host computer, receives the first sampled data from the wireless base communication port.

U.S. Pat. No. 9,574,442 for a "Hydrocarbon Well Performance Monitoring System," issued on Feb. 21, 2017 to inventor James N. McCoy, provides for a method for real-time data acquisition and presentation of force, position, load, pressures, and movement within a subterranean well pumping system, such as an oil well. Data is gathered using sensors attached to a surface level pump drive and wellhead system. Well structural data and well production data are combined therewith to generate a real-time display of downhole well operation, including animated graphics of the pump operation, including pump movement, rod and tubing stretch, fluid movement, gas compression, system forces, and fluid pressures. Liquid levels are tested using an acoustic liquid level instrument, and incorporated to improve well performance analysis.

SUMMARY OF THE INVENTION

This invention provides a drilling fluid flowback tracking system and method for determining quantities and qualities of drilling fluid returned from the wellhead in drilling operations.

The drilling fluid flowback tracking system provides a frame, a receiving pipe, a riser pipe, and a surge suppressor for conveying returned drilling fluid, a tapered fluid bin having a calibrated drain slot, which retains fluid at a level corresponding to the inflow rate of the fluid, and flow rate marks for visual correlation of the highest level of outflow with the flow rate of the inflow. Collection and retention of data is further provided through sensors in an inline sensor housing communicating through a data cable with a data collection unit. Remote access to the data collection unit is further provided through a data transceiver and remote data unit.

BRIEF DESCRIPTION OF THE DRAWINGS

Reference will now be made to the drawings, wherein like parts are designated by like numerals, and wherein.

DETAILED DESCRIPTION OF THE INVENTION

Figure 1:
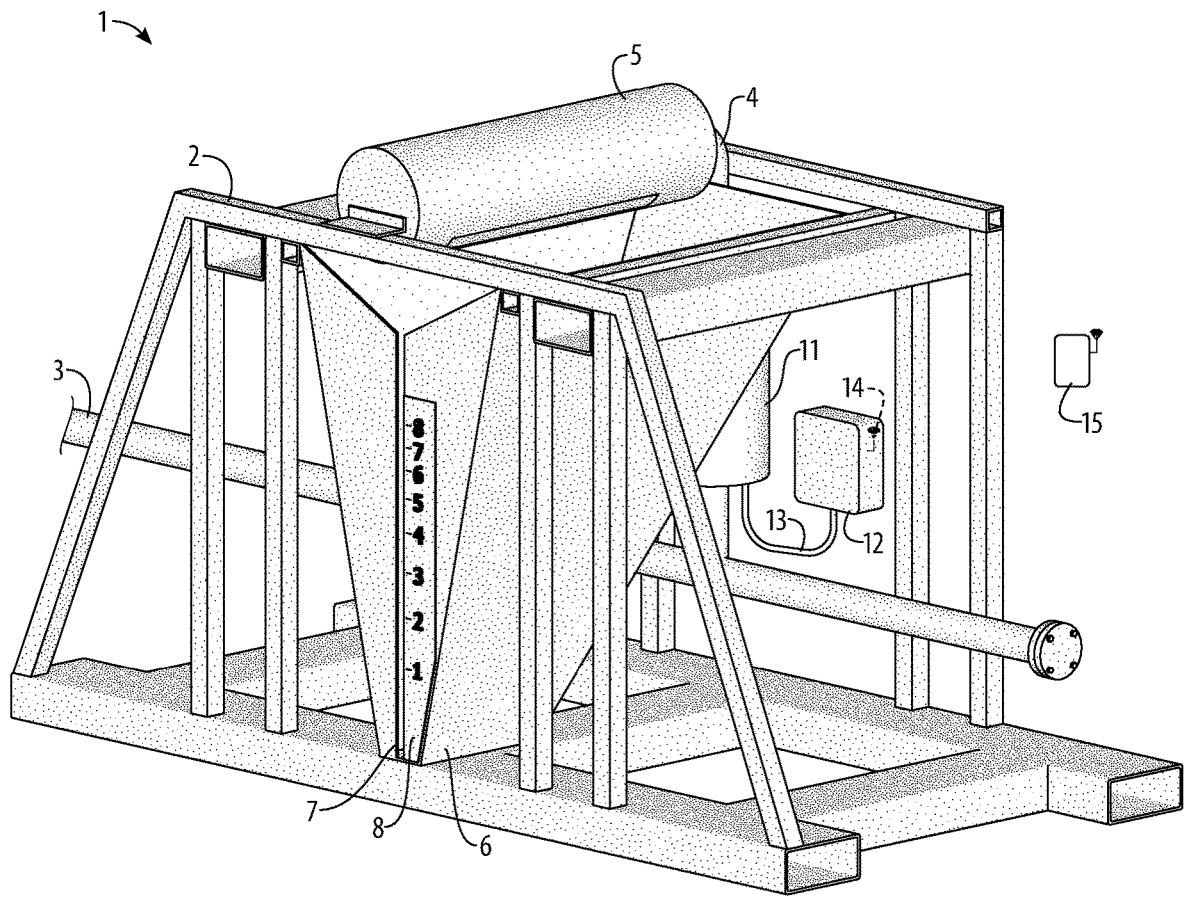
FIG. 1 is an oblique front-right view of the drilling fluid flowback tracking system of the invention.
Figure 2:
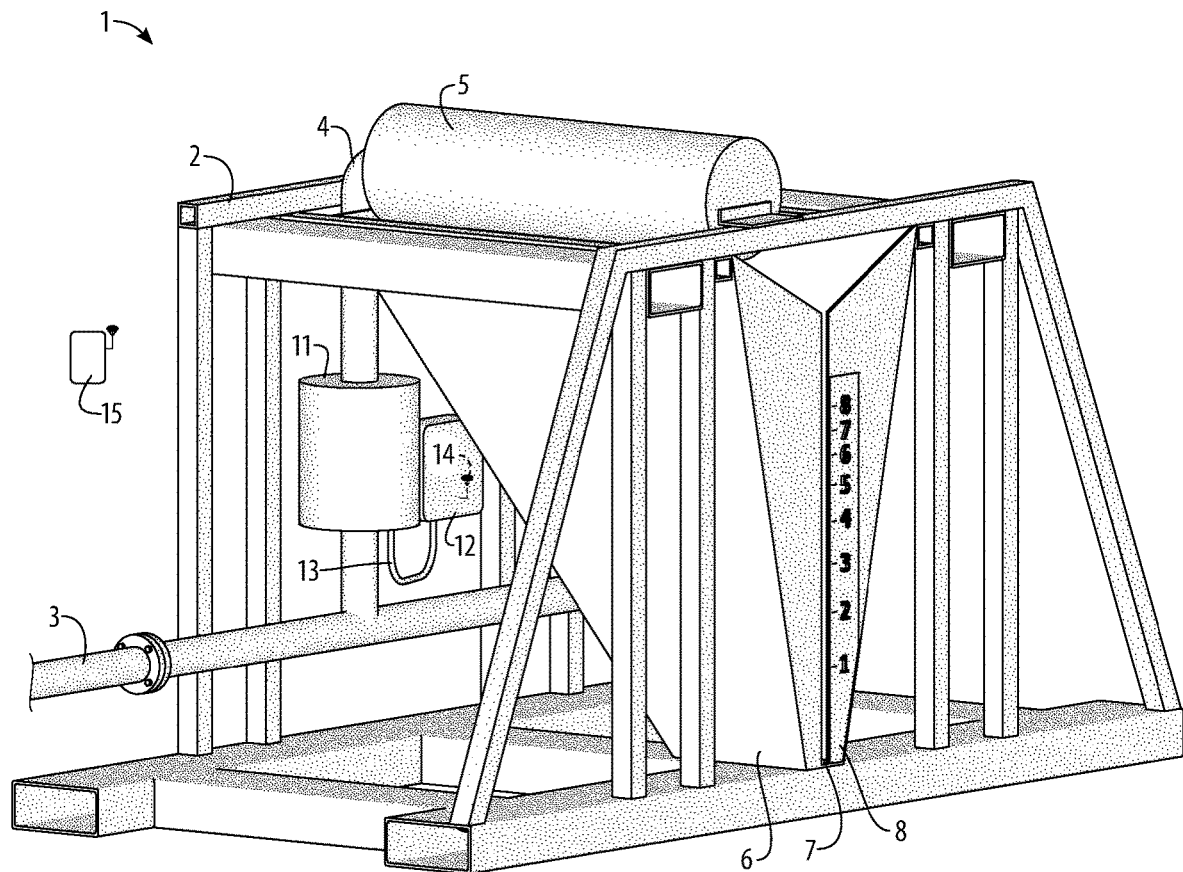
FIG. 2 is an oblique front-left view of the drilling fluid flowback tracking system of the invention.
Figure 3:
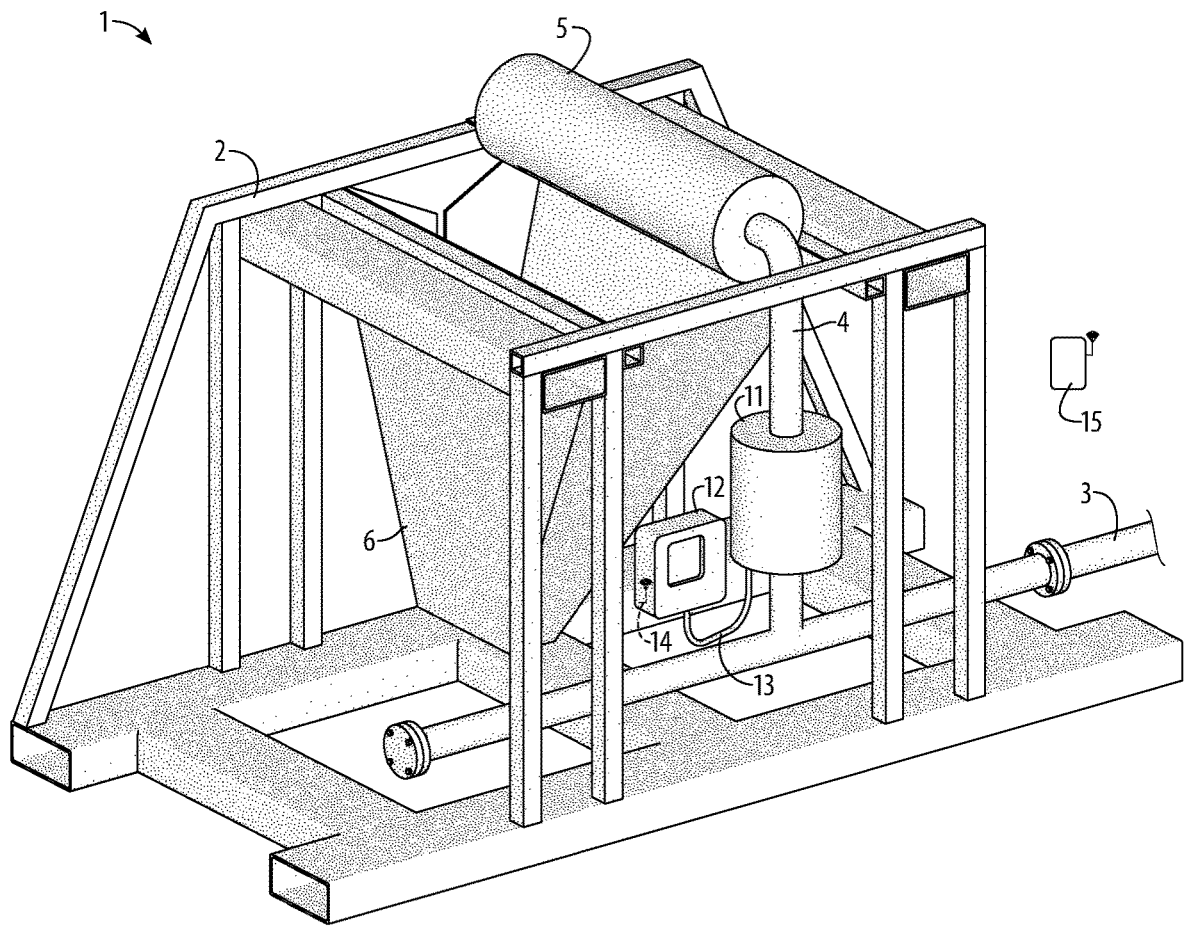
FIG. 3 is an oblique rear view of the drilling fluid flowback tracking system of the invention.
Figure 4:
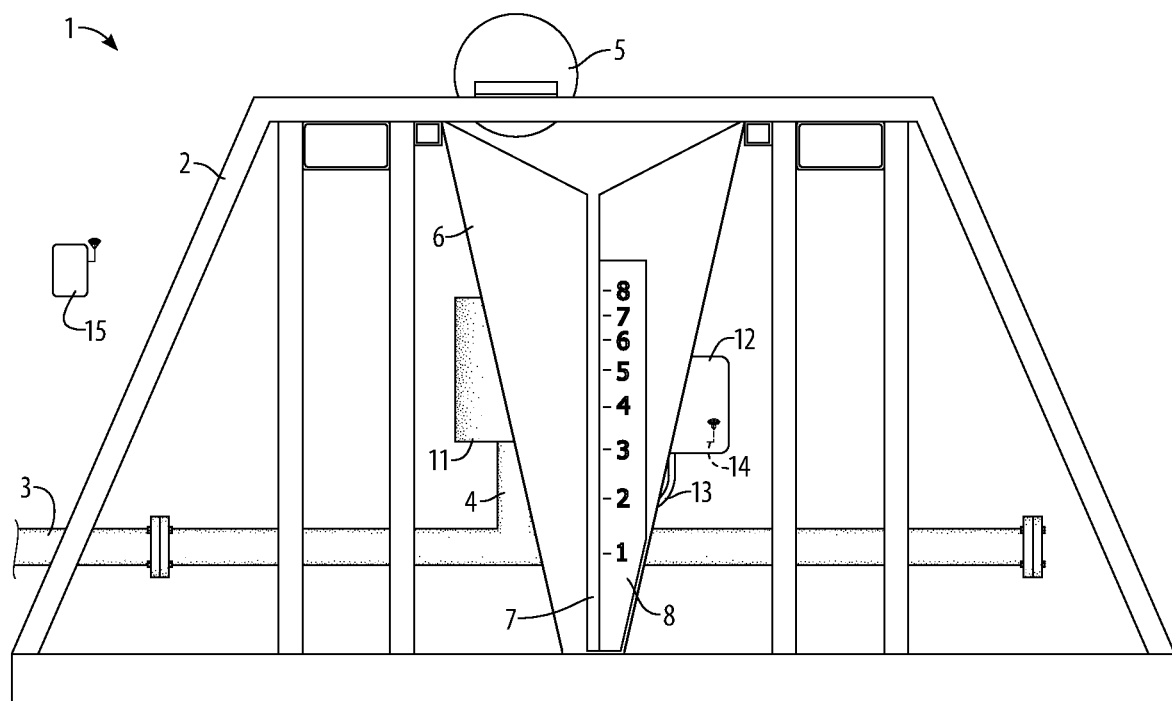
FIG. 4 is a front view of the drilling fluid flowback tracking system of the invention.
Figure 5:
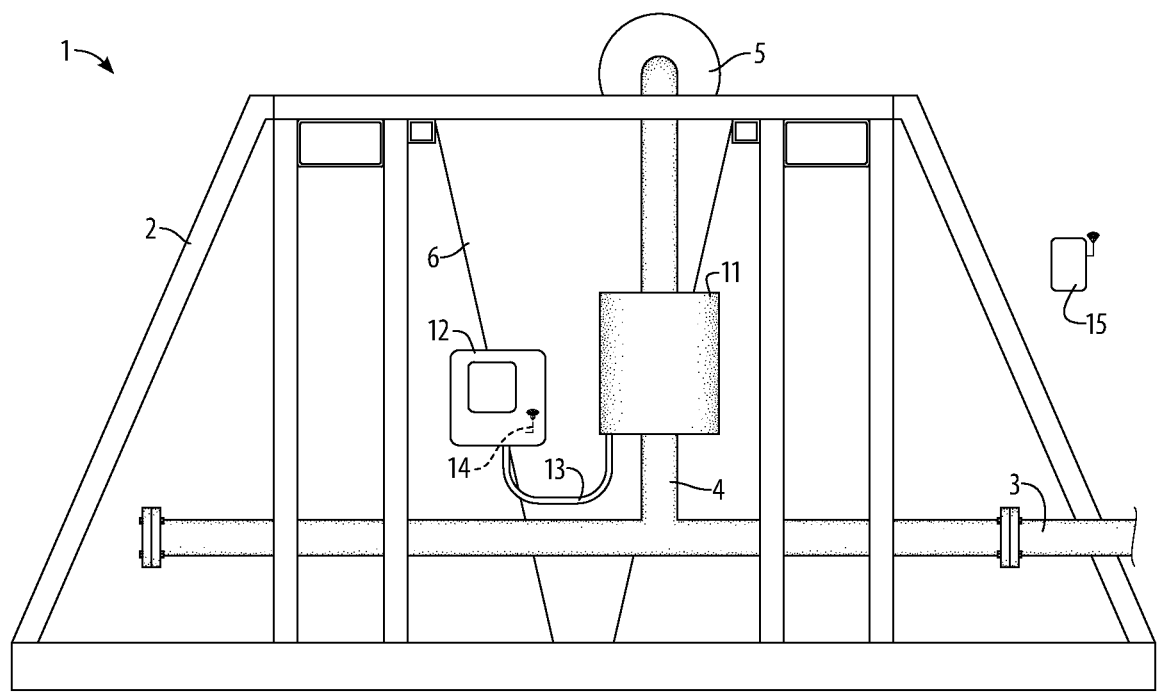
FIG. 5 is a rear view of the drilling fluid flowback tracking system of the invention.

Referring to FIGS. 1-5, the drilling fluid flowback tracking system and method 1 provides a frame 2 suited for on-site use at drilling sites and for transportation to and from drilling sites. The frame 2 provides for the lifting and mounting of the drilling fluid flowback tracking system 1 above a raised fluid recovery tank, or for use at ground level where a pond is used for fluid recovery. Mounted upon the frame is a receiving pipe 3 for receiving drilling fluid returned from the wellhead, usually through a plug or debris catcher and a choke manifold. From the receiving pipe 3 the fluid passes through a riser pipe 4, and a surge suppressor 5. The receiving pipe 3 and riser pipe 4 are sized to match the piping coming from the wellhead, plug or debris catcher, or choke, such that the pressure and velocity of the returned drilling fluid is not significantly altered. The surge suppressor 5 provides a larger volume which is open to atmospheric pressure through an opening at the bottom. When returned drilling fluid exits the smaller higher-pressure riser pipe 4 and enters the larger lower-pressure surge suppressor 5 the velocity of the returned drilling fluid will be reduced. Also, surges or kicks of pressure caused by pockets of trapped gas are contained and dissipated by the surge suppressor 5. By providing a controlled modulation of pressure at the otherwise abruptly open end of the riser pipe 4, the surge suppressor 5 prevents reflection of surges, pulses, or pressure waves, where such reflections could possibly create dangerous conditions at the termination point or upstream. The surge suppressor 5 can be provided with internal baffles to increase effectiveness. Baffles should be arranged such that they do not trap and build up any sand or debris carried by the returned drilling fluid.

The surge suppressor 5 empties returned drilling fluid through its opening at the bottom into a tapered fluid bin 6. The tapered fluid bin 6 has a trapezoidal cross-sectional profile, as shown, such that the volume of fluid accommodated at a lower level is less than the volume at a higher level. The front wall of the tapered fluid bin 6 is substantially vertical, and the other three walls are steeply sloped. The sloping walls define a contained space having less volume at the bottom than at the higher levels. The sloping walls also cause sand or debris carried by the returning drilling fluid to fall to the bottom of the tapered fluid bin 6. And the sloping walls cause fluid to flow toward the bottom, creating a flushing flow and avoiding the formation of stagnant areas where sand or debris might build up. The returned drilling fluid is ultimately discharged through the front wall of the tapered fluid bin 6 and drains into the recovery tank or pond.

Figure 6:
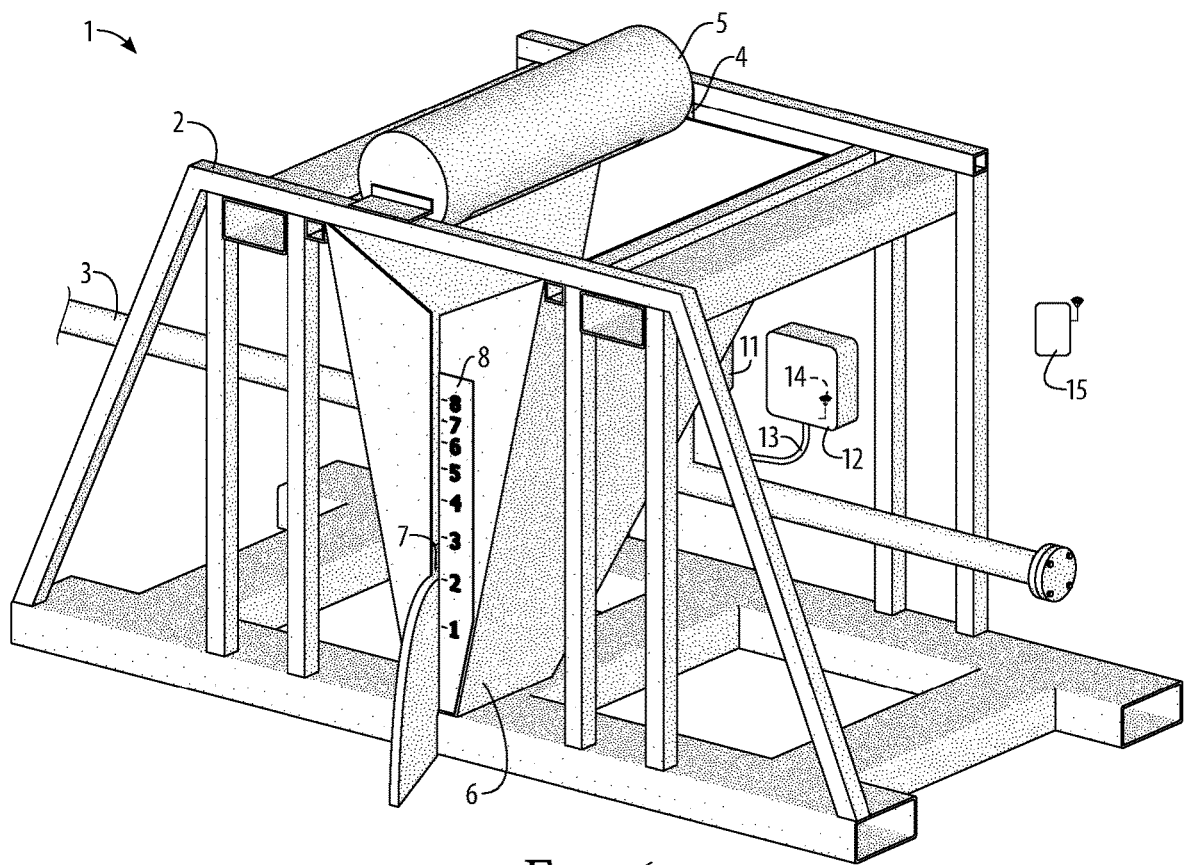
FIG. 6 is an oblique front view of the drilling fluid flowback tracking system of the invention in use, at a lower flow rate.
Figure 7:
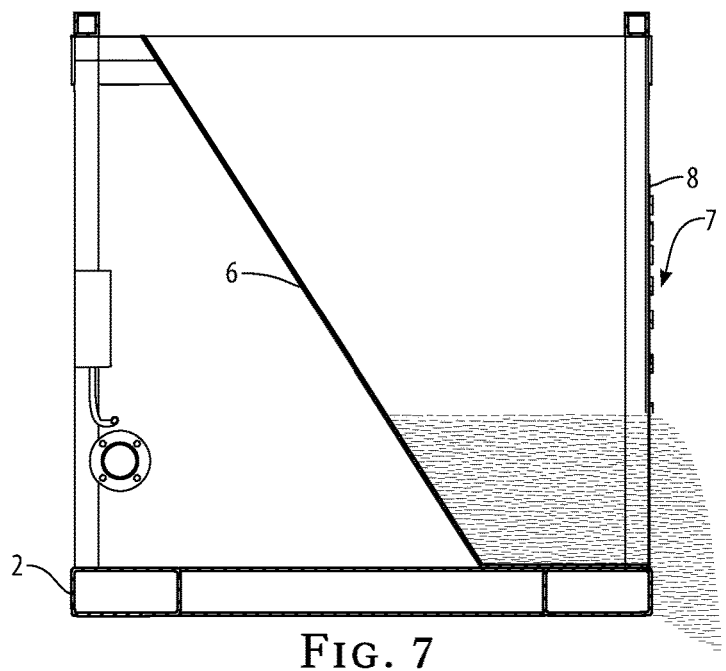
FIG. 7 is a side section view of the drilling fluid flowback tracking system of the invention in use, at a lower flow rate.
Figure 8:
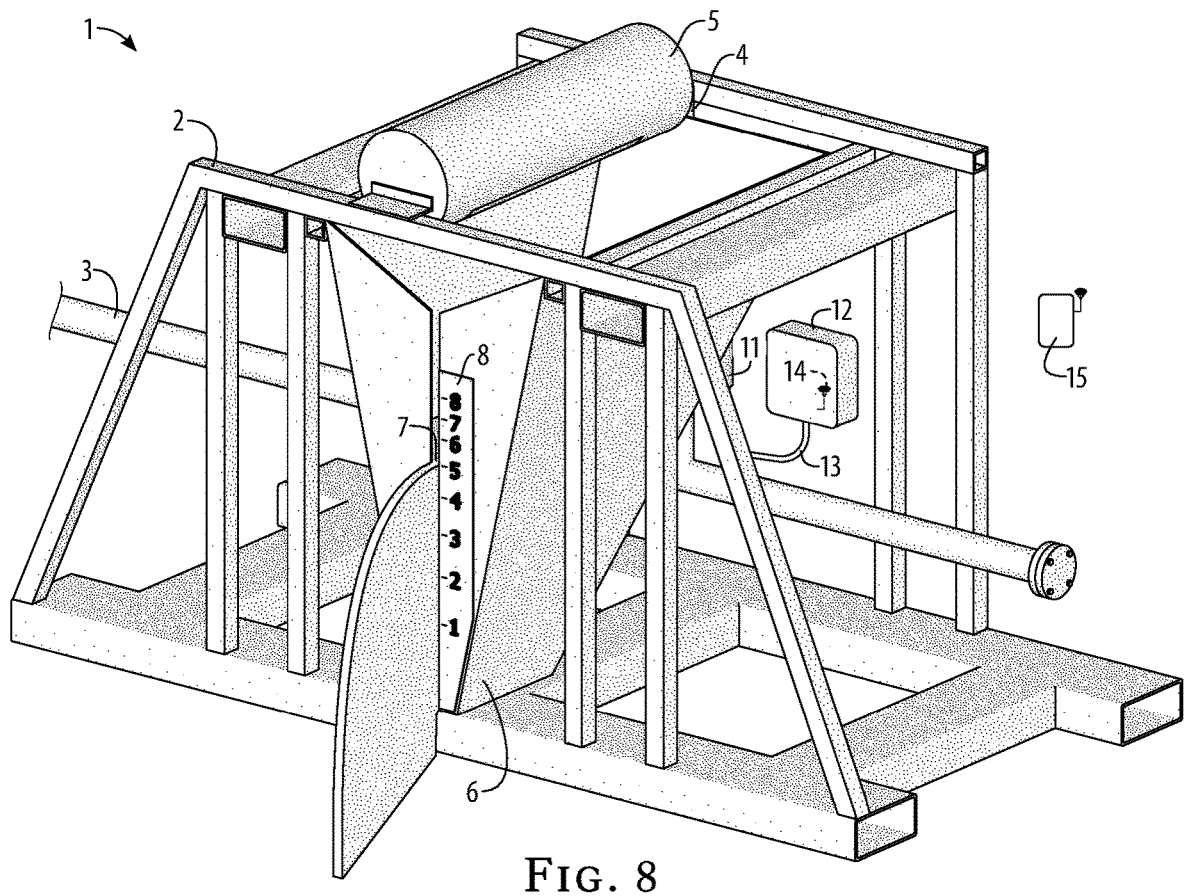
FIG. 8 is an oblique front view of the drilling fluid flowback tracking system of the invention in use, at a higher flow rate.
Figure 9:
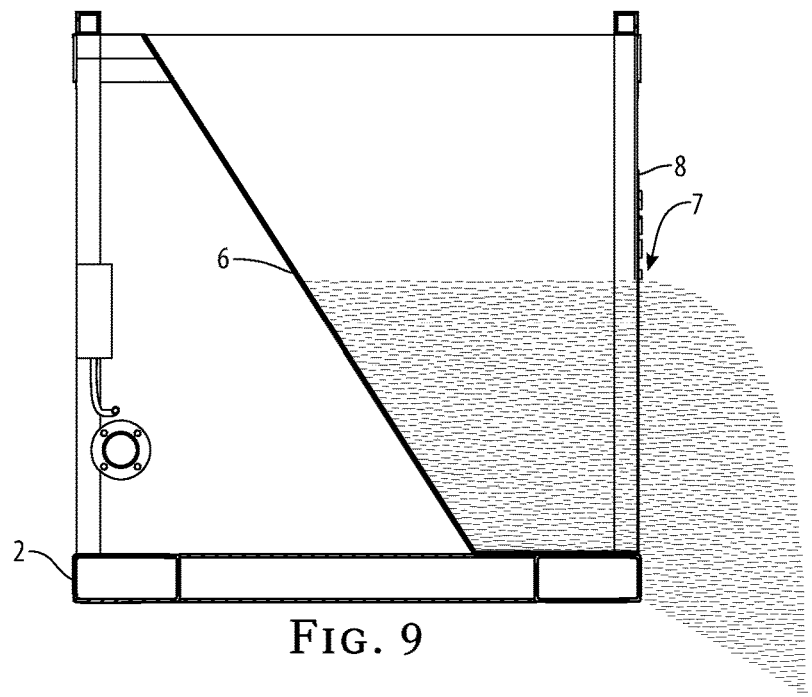
FIG. 9 is a side section view of the drilling fluid flowback tracking system of the invention in use, at a higher flow rate.

Referring to FIGS. 6-9, a calibrated drain slot 7 is provided on the front wall of the tapered fluid bin 6. The front wall is substantially vertical, and the calibrated drain slot 7 runs substantially vertically through the front wall, such that a portion of the slot is located at every potential fluid level in the tapered fluid bin 6. The calibrated drain slot is sized such that only a portion of fluid inside the tapered fluid bin 6 is allowed to drain out, and therefore the addition of more fluid at an inflow rate greater than the outflow rate through the calibrated drain slot will cause a buildup of fluid, and the fluid level in the tapered fluid bin will rise. As the fluid level in the tapered fluid bin rises, the fluid is allowed to drain through additional, higher levels of the calibrated drain slot 7, which increases the overall outflow rate. The calibrated drain slot 7 is sized such that a given steady rate of inflow will result in a corresponding steady level of backed-up fluid in the tapered fluid bin 6. The backed-up fluid will flow through the calibrated drain slot 7 from the bottom up to the level of the backed-up fluid in the tapered fluid bin 6. The highest level of fluid exiting the calibrated drain slot 7 equals the level of backed-up fluid in the tapered fluid bin 6, which in turn corresponds to a specific inflow rate from the surge suppressor 5, riser pipe 4, receiving pipe 3, and ultimately back to the wellhead.

An indication of flow rate marks 8 is provided on the tapered fluid bin 6 near the calibrated drain slot 7 so that quick real-time visual determinations of flow rate can be made. For persons not on site or not in sight of the drilling fluid flowback tracking system 1, a feed from a remote video camera might be used, or data from the data collection unit 22, disclosed below, might be used.

Referring again to FIGS. 1-5, data about the returned drilling fluid, such as pressure, flow rate, temperature, viscosity, pH, and density of dissolved components can be determined by sensors placed into or near the line of flow. Such data can be used in real time to monitor and inform actions taken on-site. Also, such data, or additional data derived from it, can be used to analyze past events or to confirm such things as the quantity of water recovered compared with billing for quantities of water hauled away.

An embodiment of the drilling fluid flowback tracking system 1 provides for the recording and reporting of such data. An inline sensor housing 11 is incorporated into the riser pipe 4. One or more sensors can be mounted within the inline sensor housing 11. Data from the sensors is transmitted to a data collection unit 12 through a data cable 13. The data collection unit 12 captures and stores the received data in electronic form. Optionally, the data collection unit 12 can display real-time or recent historical data on a screen or printout. The stored data can be exported from the data collection unit 12 for analysis and long-term storage.

Because of the harsh operating environment, the data collection unit 12 should be made with components able to operate in the environment, should be contained in a rugged enclosure, and should be removable. A related embodiment also provides a data transceiver 14 and remote data unit 25 providing for wireless remote communications. The data transceiver 14 is incorporated into the data collection unit 12. The remote data unit 25 communicates with the data collection unit 12 through the data transceiver 14. The remote communications can occur within the drilling or workover site and, if the required network service is available, over a wider communications network. Optionally, the remote data unit 15 can be implemented on a smartphone, tablet, or laptop computer device.

Many other changes and modifications can be made in the system and method of the present invention without departing from the spirit thereof. I therefore pray that my rights to the present invention be limited only by the scope of the appended claims.

I claim:

1. A tracking system for drilling fluid returned from a well, comprising:
   (i) a portable frame configured for removable positioning above a well and configured to receive drilling fluid returned from a wellhead:
   (ii) an inline sensor housing mounted upon said frame in line on a drilling fluid return pipe, adapted to house at least one sensor for sensing quantities, volume, and qualities of returned drilling fluid;
   (iii) a removable data collection unit connected to said inline sensor housing through a data cable, adapted to receive, store, and manage data from sensors within said inline sensor housing, said data collection unit having a rugged enclosure capable of operating in hazardous environment; (iv) a data transceiver incorporated into said data collection unit, adapted to provide wireless communications with said data collection unit; and
   (v) a remote data unit adapted to communicate with said data collection unit through said data transceiver and analyze the quantities, volume, and qualities of the returned drilling fluid as compared with the quantity, volume and qualities of the drilling fluid pumped into the well.

2. The tracking system of claim 1, where said inline sensor housing is further adapted to house an electronic flow rate sensor.

3. The tracking system of claim 1, where said inline sensor housing is further adapted to house a mechanical flow rate sensor.

4. The tracking system of claim 1, where said inline sensor housing is further adapted to house a viscosity sensor.

5. The tracking system of claim 1, where said inline sensor housing is further adapted to house a pressure sensor.

6. The tracking system of claim 1, where said inline sensor housing is further adapted to house a temperature sensor.

7. The tracking system of claim 1, where said inline sensor housing is further adapted to house a pH sensor.

8. The tracking system of claim 1, where said inline sensor housing is further adapted to house a dissolved-material sensor.

9. A method of tracking quantity, volume, and properties of drilling fluid returned from a well, comprising the steps of:

(i) providing a tracking system comprising:
  (a) a portable frame configured for removable positioning above a well and configured to receive drilling fluid returned from a wellhead:
  (b) an inline sensor housing mounted upon said frame in line on a drilling fluid return riser, the sensor housing adapted to house at least one sensor for sensing quantities, volume, and properties of returned drilling fluid;
  (c) a removable data collection unit connected to said inline sensor housing through a data cable, adapted to receive, store, and manage data from sensors within said inline sensor housing, said data collection unit having a rugged enclosure capable of operating in hazardous environment;
  (d) a data transceiver incorporated into said data collection unit, adapted to provide wireless communications with said data collection unit; and
  (e) a remote data unit adapted to communicate with said data collection unit through said data transceiver;
(ii) connecting the tracking system to the return fluid riser;
(iii) collecting data generated by the tracking system; and
(iv) analyzing the quantities, volume, and properties of the returned drilling fluid as compared with the quantities, volume and properties of the drilling fluid pumped into the well.

\* \* \* \* \*